United States Patent [19]

Sano et al.

[11] 4,121,988

[45] Oct. 24, 1978

[54] OXYGEN SENSOR

[75] Inventors: Hiromi Sano, Nagoya; Masatosi Suzuki, Kariya, both of Japan

[73] Assignee: Nippondenso Co., Ltd., Japan

[21] Appl. No.: 746,632

[22] Filed: Dec. 1, 1976

[30] Foreign Application Priority Data

Dec. 19, 1975 [JP] Japan .................. 50-152337
Sep. 8, 1976 [JP] Japan .................. 51-108105

[51] Int. Cl.² .......................................... G01N 27/46
[52] U.S. Cl. .......................... 204/195 S; 123/119 E
[58] Field of Search .................... 204/1 S, 195 S; 123/119 C

[56] References Cited

U.S. PATENT DOCUMENTS

| 3,768,259 | 10/1973 | Carnahan et al. | 204/195 S |
| 3,773,641 | 11/1973 | Fitterer | 204/195 S |
| 3,935,089 | 1/1976 | Togawa et al. | 204/195 S |
| 4,021,326 | 5/1977 | Pollner et al. | 204/195 S |

FOREIGN PATENT DOCUMENTS

| 870,223 | 5/1971 | Canada | 204/195 S |
| 1,511,066 | 12/1967 | France | 204/195 S |
| 1,081,545 | 8/1967 | United Kingdom | 204/195 S |

*Primary Examiner*—T. Tung
*Attorney, Agent, or Firm*—Cushman, Darby & Cushman

[57] ABSTRACT

An oxygen sensor for detecting an oxygen concentration in exhaust gas such as that exhausted from an internal combustion engine, said sensor comprising a solid electrolyte made of an oxygen ion conducting metal oxide which is subjected to gas to be monitored and reference gas, e.g., atmosphere and generating an e.m.f. which corresponds to a difference between oxygen concentrations of both gases. Said solid electrolyte has conductive ribs acting as an auxiliary electrode strongly bonded to that surface thereof which is subjected to the exhaust gas.

16 Claims, 25 Drawing Figures

OXYGEN SENSOR

BACKGROUND OF THE INVENTION

1. Field of the Invention

The present invention relates to an oxygen sensor which detects an oxygen concentration or the presence or absence of oxygen in a gas component of a gas to be monitored, and more particularly to a solid electrolyte having an improved durability.

2. Description of the Prior Art

Heretofore, as taught in the U.S. Pat. No. 3,759,232 and the SAE Paper No. 750,368, published in February, 1975, it has been proposed to use an oxygen sensor to detect oxygen concentration in exhaust gas exhausted from an internal combustion engine in order to control the air-fuel ratio of a mixture to be supplied to the internal combustion engine. The oxygen sensor has a solid electrolyte which is made of an oxygen ion conducting metal oxide or solid electrolyte which generates an e.m.f. corresponding to a difference between an oxygen concentration or an oxygen partial pressure of a gas component of a gas to be monitored and an oxygen concentration or an oxygen partial pressure of a reference gas (e.g. atmosphere). On that surface of the solid electrolyte which is subjected to the reference gas, a thin film platinum electrode is formed by chemical plating, vacuum deposition or the like, and on that surface of the solid electrolyte which is subjected to the gas to be monitored, a thin film platinum electrode is also formed so that the e.m.fs generated at both electrodes of the solid electrolyte are taken.

However, the oxygen sensor of the type described above includes a disadvantage that extended use thereof results in deterioration of performance such that a sufficient e.m.f. to allow precise control of the air-fuel ratio cannot be taken.

After extensive study on the above problem, the inventors of the present invention have found that the cause of the above problem was that the thin film electrode on that surface of the solid electrolyte which was subjected to the gas to be monitored was exposed to that gas whenever the detector was used, and when the temperature variation of the gas was remarkable such as in the case of exhaust gas exhausted from the internal combustion engine, the electrode was consumed and peeled away in a short time because it was a thin film. Discussing the problem in further detail, in addition to the thin film structure of the electrode, the fact that the electrode and the solid electrolyte are made of different materials and the adherence therebetween is poor has a significant affect. The consumption and the peel-off of the electrode occur e.g. at the center of the electrode and they result in non-conduction among non-consumed or non-peeled portions of the electrode. As a result, a sufficient e.m.f. cannot be taken out.

SUMMARY OF THE INVENTION

It is an object of the present invention to overcome the above drawbacks and to improve the durability of an oxygen sensor.

It is another object of the present invention to provide an oxygen sensor which permits a sufficient e.m.f. output even if a thin film electrode thereof is partially consumed or peeled away.

An oxygen sensor according to the present invention comprises a sintered structure of particles of conductive metal and heat resisting bonding material such as glass frits or metal oxide frits. A wire-shaped conductive rib is rigidly attached on that surface of the solid electrolyte which is subjected to the gas to be monitored by the heat resisting bonding material in the sintered structure. Thin film electrodes of conductive metal are provided on an outer surface of the rib and on that surface of the solid electrolyte which does not carry the rib, respectively. The rib functions as an auxiliary electrode.

According to the present invention, since both the wire-shaped rib and the thin film electrode are made of conductive metal, the adherence therebetween is strong. The consumption and the peel-off of that portion of the thin film electrode which is attached to the rib are suppressed. Since the rib is rigidly and strongly bonded to the surface of the solid electrolyte by the glass frits or metal oxide included in the sintered structure, it is hardly consumed or peeled off. Although that portion of the thin film electrode which is not attached to the rib may be consumed or peeled off, or that portion of the thin film electrode which is attached to the rib might be partially consumed or peeled off because of its thin film structure, the rib which is strongly bonded to the solid electrolyte serves as the auxiliary electrode to provide electrical conduction among non-consumed and non-peeled portions of the thin film electrode. As a result, the prior problem of lack of ability of providing a sufficient e.m.f. output over an extended period of use has been resolved and a solid electrolyte having an improved durability has now been provided.

BRIEF DESCRIPTION OF THE DRAWINGS

FIG. 21 shows characteristic curves illustrating a relation between an air excess rate and an e.m.f., in which

FIG. 22 shows characteristic curves illustrating a relation between a temperature of exhaust gas and an e.m.f., in which

DESCRIPTION OF THE PREFERRED EMBODIMENTS

The present invention is now explained in detail in conjunction with the preferred embodiments thereof for detecting an air-fuel ratio of an internal combustion engine.

Figures 1, 2, 3, 4, 5:
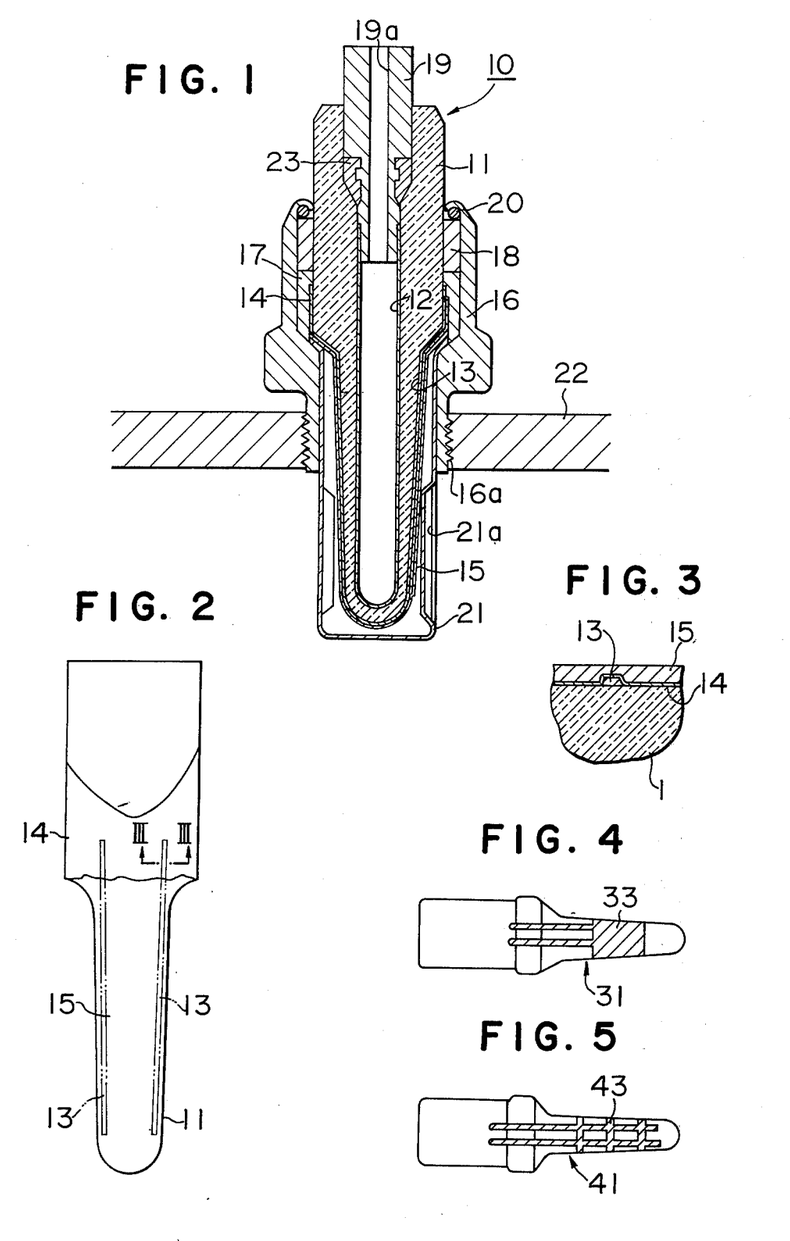
FIG. 1 is a front sectional view illustrating one embodiment of an oxygen sensor of the present invention.
FIG. 2 is a front view of a solid electrolyte in the oxygen sensor of FIG. 1.
FIG. 3 is a sectional view taken along a line III—III in FIG. 2.
FIGS. 4 to 7 show second to fifth embodiments of the present invention, respectively, illustrating the solid electrolyte having different ribs formed thereon.

Referring to FIGS. 1 to 3 which show a first embodiment of the present invention, numeral 10 denotes an oxygen sensor which has an overall configuration similar to that of a conventional spark plug. A solid electrolyte 11 is formed by a fine sintered structure of an oxygen ion conducting metal oxide consisting of 85 mole % of $ZrO_2$ and 15 mole % of CaO solid solution. Alternatively, it may consist of $ZrO_2$, $ThO_2$ or $CeO_2$ and divalent or trivalent CaO, $Y_2O_3$ or MgO. A composition of 90-92 mole % of $ZrO_2$ and 10-8 mole % of $Y_2O_3$ is particularly suitable in that it improves conductivity and allows conduction of oxygen ions even at a relatively low temperature, that is, it widens a range of operation temperature for the solid electrolyte. The solid electrolyte 11 is of cup-shape with one end thereof being open and the other end being closed. However, it should be understood that the shape of the solid electrolyte 11 need not be limited to the cup-shape but it may be any other shape such as disc-shape or cylinder shape (hollow) depending on the particular applications. Formed on an inner wall of the solid electrolyte 11 is a first electrode 12 of platinum porous thin film of the thickness of about 1 to 2 microns, by chemical plating technique. On an outer wall of the solid electrolyte 11, there are formed four wire-shaped conductive ribs 13, which are formed by applying and firing paste consisting of a mixture of particles of platinum and frits of low melting point glass such as borosilicate glass. The ribs 13 extend from those points which lie 5 mm inside the closed edge of the solid electrolyte 11 over a distance of about 35 mm. The ribs 13 may be formed by preparing mixture consisting of 80% by volume of platinum particles (having particle size of 2 microns) and 20% by volume of borosilicate glass frits acting as heat resisting bonding material, adding organic solvent thereto to form a paste, applying the paste on the outer wall of the solid electrolyte 11 by thin film printing technique or dipping method, and firing the assembly at 1000° to 1200° C. Through the firing, the ribs 13 are strongly bonded to the surface of the oxygen concentration detector 11 partially through the borosilicate glass. The thickness of the ribs 13 may be about 20 microns. While the paste for forming the ribs 13 in the above embodiment consists of the platinum particles and the glass frits, it should be understood that frits of metal oxide such as $ZrO_2$ or $Al_2O_3$ (alumina) may be used instead of the glass frits, as the heat resisting bonding material. In this case, during the firing step of the paste, the metal oxide included therein reacts with the solid electrolyte 11 to assure strong bonding of the ribs 13 to the solid electrolyte 11.

The composition of the paste consisting of the platinum particles and the glass frits or the metal oxide frits preferably includes 55 to 95% by volume of platinum particles and the balance of, i.e. 45 to 5% by volume of glass frits or metal oxide frits. When the proportion of the glass frits or the metal oxide frits is too high, the ribs 13 will lose the conductivity. The platinum particles preferably have particle size of 2 microns. On that surface portion of the outer wall of the solid electrolyte 11 on which the ribs 13 are not formed and on the outer surfaces of the rib 13, there is formed a second electrode 14 of platinum porous thin film of the thickness of about 1 to 2 microns, which film is formed by a dual chemical and electrical plating method. Formed on the surface of the second electrode 14 is an insulating coating 15 of the thickness of 50 to 200 microns made of a porous $\alpha$-alumina ($Al_2O_3$) which is heat resisting and permits the transmission of exhaust gas exhausted from an internal combustion engine, not shown. While the first electrode 12 and the second electrode 14 are shown to be made of platinum, they may be made of other material having heat resisting and anti-corrosion properties as well as catalytic action, such as Pd, Au, Ag, or even alloys thereof. The same consideration is applicable to the conductive metal particles included in the ribs 13.

The material of the heat resisting, porous, insulating coating 15 formed on the surface of the second electrode 14 is not limited to $Al_2O_3$ but it may be silicate of $ZrO_2$, MgO, $CaSiO_3$, MgO, $Al_2O_3$, $MgAl_2O_4$ of spinel structure, or composite oxide thereof, carbonate, nitrate or borate of metal, feldspar, kaolin or sintered glass. Depending on the particular applications, the use of the materials having catalytic action may not be required for the first electrode 12, the second electrode 14 and the ribs 13.

Housing 16 is of cylinder shape and disposed around the outer wall of the solid electrolyte 11. The housing 16 has a threaded portion 16a. Between the housing 16 and the outer wall of the solid electrolyte 11, a ring 17 of conductive graphite and a ring 18 are arranged. By pressing the ring 18 from the top thereof, the conductive graphite ring 17 is firmly fixed between the housing 16 and the solid electrolyte 11. Numeral 19 denotes an inner shaft. A conductive graphite ring 23 is disposed between the inner shaft 19 and the inner wall of the solid electrolyte 11, and the conductive graphite ring 23 is firmly fixed when the inner shaft 19 is pressed from the top thereof. The inner shaft 19 has an axial bore 19a through which the inner wall of the solid electrolyte 11 is exposed to an atmosphere which serves as a reference gas. Numeral 20 denotes a calking or tightening O-ring which is disposed on the ring 18. After the O-ring 20 has been positioned in place, an entire external periphery of the housing 16 is calked or sealed so that the housing 16 and the solid electrolyte 11 are fixed relative to each other. Numeral 21 denotes a protection tube fixed (by welding or the like) to the inner wall of the housing 16 at the bottom thereof. It has a cylindrical shape to surround that surface of the solid electrolyte 11 which is subjected to the exhaust gas. The protection tube 21 is formed with an cutout opening 21a through which the exhaust gas flowing in an exhaust tube 22 is brought into contact with the solid electrolyte 11. The opening 21a may be formed by blanking. The ribs 13 and the second electrode 14 on the outer wall of the solid electrolyte 11 electrically connect to the housing 16 through the conductive graphite ring 17. The first electrode 12 on the inner wall of the solid electrolyte 11 electrically connects to the inner shaft 19 directly or through the conductive graphite ring 23. Thus, the housing 16 and the inner shaft 19 function as terminals from which an e.m.f. representing the oxygen concentration is taken out.

The operation of the oxygen (concentration) sensor 10 thus constructed in now explained. The assembly of the oxygen sensor 10 is screwed into the exhaust pipe 22 of the internal combustion engine by the thread 16a of the housing 16 so that the solid electrolyte 11 is exposed to the exhaust gas. As is well known, the exhaust gas includes component gases such as $O_2$, CO and HC (hydrocarbon) and the concentrations of these component gases change depending on an air-fuel ratio of air-fuel mixture before combustion.

The solid electrolyte 11 generates an e.m.f. corresponding to a difference between an oxygen concentration or an oxygen partial pressure of the component gases in the exhaust gas and an oxygen concentration or an oxygen partial pressure of an atmosphere which serves as reference gas. By the catalytic action of the platinum of the ribs 13 and the second electrode 14 formed on that surface of the solid electrolyte 11 which is subjected to the exhaust gas, the $O_2$ in the component gases contributes to the oxidization of CO and HC on that surface of the solid electrolyte 11 which is subjected to the exhaust gas. At an air-fuel ratio which is richer than a stoichiometric air-fuel ratio, the amount of CO and HC is more than that of $O_2$ and the oxygen concentration in the component gases on that surface of the solid electrolyte 11 which is subjected to the exhaust gas is low or zero. At an air-fuel ratio which is leaner than a stoichiometric 1, the amount of CO and HC is less than that of $O_2$ and the oxygen concentration in those component gases is high or has a definite value. As a result, the e.m.f. generated by the oxygen concentration detector 11 changes abruptly around the stoichiometric air-fuel ratio. Thus, by setting the e.m.f. corresponding to the stoichiometric air-fuel ratio as a reference voltage and comparing a detected e.m.f. corresponding to the actual air-fuel ratio, the air-fuel ratio richer than the stoichiometric one is indicated when the detected e.m.f. is higher than the reference voltage and the air-fuel ratio leaner than the stoichiometric one is indicated when the detected e.m.f. is lower than the reference voltage. In this manner, it is possible to maintain the air-fuel ratio at the stoichiometric 1. As is well known, it is around the stoichiometric air-fuel ratio that a three-way catalyst converter can convert noxious component gases in the exhaust gas, i.e. CO, HC and $NO_x$ gases into innoxious components at high efficiency. Therefore, in an internal combustion engine of an automobile, it is very effective in preventing air pollution to control the air-fuel ratio of the mixture to the stoichiometric ratio.

The solid electrolyte 11 is exposed to the exhaust gas whenever the oxygen sensor 10 is used. As is well known, the temperature of the exhaust gas changes over a wide range and hence that surface of the solid electrolyte 11 which is subjected to the exhaust gas is put in the direct influence of cooling-heating cycle by the exhaust gas. Since the ribs 13 are made by sintering the paste of the mixture of the platinum particles and the borosilicate glass frits, the borosilicate glass frits melt during the sintering step to enhance the adherence between the surface of the solid electrolyte 11 and the platinum particles. As a result, the bonding between the ribs 13 and the oxygen concentration detector 11 after the sintering is strong. Accordingly, the ribs 13 are not peeled off the solid electrolyte 11 when they are subjected to the cooling-heating cycle. Furthermore, since the material of the ribs 13 and the material of the second electrode 14 are the same, i.e. platinum, the adherence between the ribs 13 and the second electrode 14 is also strong. In addition, those portions of the second electrode 14 on which the ribs 13 are bonded are further protected against peel-off.

However, because of the thin film structure of the second electrode 14, during an extended use under the cooling-heating cycle, those portions of the second electrode 14 on which the ribs 13 are bonded may be gradually consumed although those portions are protected, to a certain extent, against the peel-off. Furthermore, that portion of the second electrode 14 on which the ribs 13 are not bonded may also be consumed and peeled off. That portion of the second electrode 14 which is subjected to violent consumption and peel-off is the portion which faces the opening 21a of the protection 21 and to which the exhaust gas directly impinges, and the portions of the solid electrolyte 11 near the closed end thereof and the portions inside the housing 16 are not subjected to violent consumption and peel-off. However, if the second electrode 14 is consumed or peeled off even partially, it loses its function as the electrode, because the partial consumption or peel-off of the second electrode 14 results in the loss of electrical conduction between the remaining unconsumed or non-peeled areas thereof.

However, by the provision of the ribs 13 strongly bonded to the solid electrolyte 11, electric conduction between the non-consumed and non-peeled areas of the second electrode 14 is assured and an e.m.f. can be effectively taken out.

In essence, even if the second electrode 14 is partially consumed or peeled off, the conductivity of the second electrode 14 is maintained by the conductive ribs 13 which, in this case, serve as an auxiliary electrode.

Since the insulating coating 15 is formed on the outer surface of the second electrode 14, the second electrode 14 can be protected from noxious components in the exhaust gas, such as P, S, Pb. It has been proven by an experiment by the inventors that if those noxious components should deposit and accumulate on the surface of the second electrode 14, the performance of the latter would be deteriorated such that the catalytic action described above is diminished or the e.m.f. could not be effectively taken out.

By forming the insulating coating 15 on the surface of the second electrode 14, however, the chance of the noxious components contacting with the second electrode 14 is reduced. That is, the insulating coating 15 functions as a filter. Since the insulating coating 15 is porous and permits the transmission of the exhaust gas therethrough, there is no influence on the measurement of e.m.f.

Figure 6:
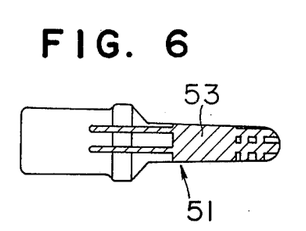
Figure 7:
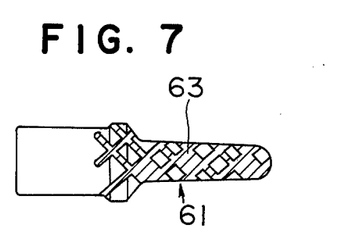

FIGS. 4 to 7 show second to fifth embodiments of the present invention, respectively with the shape of the ribs being modified in various ways. In the second embodiment shown in FIG. 4, the rib comprises a ring-shaped portion formed at a center of a tip end of a solid electrolyte 31 and four wire-shaped portions extending therefrom. The third embodiment of FIG. 5 shows a grid-like structure, and the fourth embodiment of FIG. 6 shows a similar structure as that of FIG. 4 with the addition of grid-like portion at a tip end of a solid electrolyte 51, and the fifth embodiment of FIG. 7 shows a net-like structure. In those drawings, numerals 41, 51, 61 denote the solid electrolyte and 33, 43, 53, 63 denote the ribs having different shapes.

While the ribs are formed by applying and firing the paste in the previous embodiments, they may be formed by embedding wire elements as described hereinafter.

Referring to FIGS. 8 to 11 which illustrate a sixth embodiment of the present invention, a first thin film electrode 72 is formed by chemical plating method, vacuum deposition or the like, as in the case of FIG. 1, on an inner wall of a cup-shaped solid electrolyte 71. On an outer surface thereof, a second thin film electrode 73 is formed in a similar method. Provided on the outer wall of the solid electrolyte 71 is a third electrode 74 of platinum wire having a diameter of 0.3 mm and a length of 32 mm. The third electrode 74 is embedded in a groove 71a which extends from an closed end to an intermediate portion of the solid electrolyte 71. The third electrode 74 is embedded during the manufacture of the solid electrolyte 71. In the manufacturing process, 85 mole % of $ZrO_2$ and 15 mole % of CaO are mixed and the resulting mixture is ground and, after calcination it is formed into the the cup-shape and at the same time a groove 71a' having a depth of 0.3 mm, a width of 1.5 mm and a length of 32 mm is formed. The cup-shaped structure and the groove may be formed simultaneously by a known rubber press forming method. The third electrode 74 which has been previously bent to fit the outer surface of the cup-shaped molded structure 71' is then embedded in the groove 71a' of the structure 71' so that it is held by the structure. The assembly is then fired at a temperature between about 1600° and 1750° C. to complete the solid electrolyte 71. Because of shrinkage during the firing step, the third electrode 74 is held in the groove 71a without being removed and is finally embedded therein.

Figure 8:
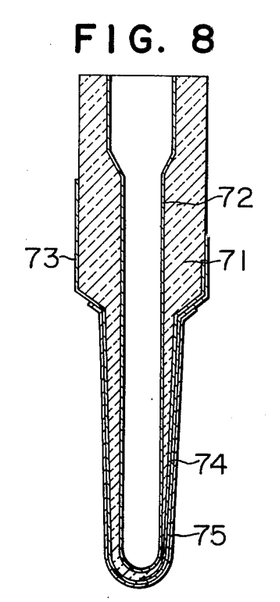
FIG. 8 is a front sectional view showing major parts of a sixth embodiment of the present invention.
Figure 9:
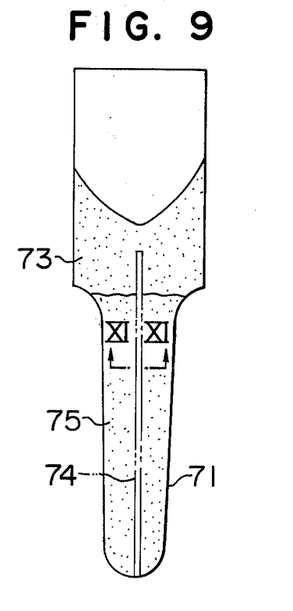
FIG. 9 is a front view showing an oxygen concentration detector of the oxygen sensor of FIG. 8.
Figure 10:
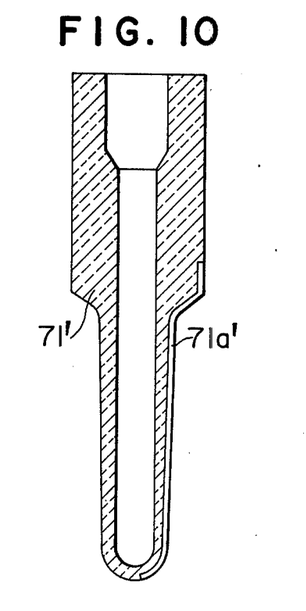
FIG. 10 is a front sectional view showing a molded structure in a manufacturing step of the solid electrolyte of FIG. 9.
Figure 11:
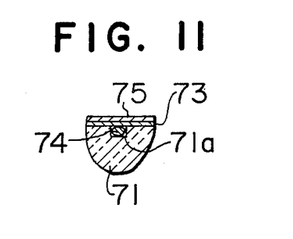
FIG. 11 is a sectional view taken along a line XI—XI in FIG. 9.

The first electrode 72 and the second electrode 73 are formed after the third electrode 74 has been embedded in the solid electrolyte 71. The second electrode 73 is formed over the surface of the third electrode 74.

The surface of the second electrode 73 is coated with a porous coating 75 of $\alpha$-$Al_2O_3$ which is heat resisting and permits transmission of exhaust gas exhausted from the internal combustion engine.

Figure 12:
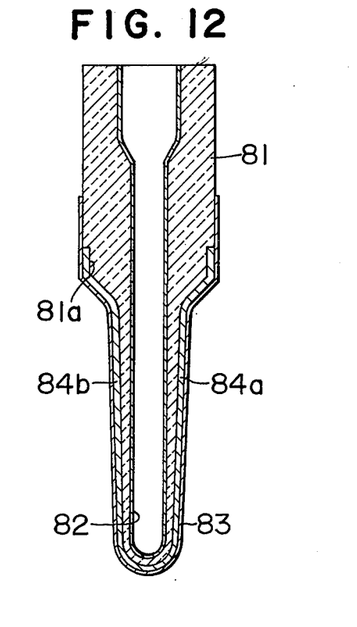
FIG. 12 is a front sectional view showing an oxygen concentration detector in a seventh embodiment of the present invention.

FIG. 12 shows a second embodiment of the present invention in which a pair of third electrodes 84a, 84b of platinum wire are provided in opposing relation to each other on that surface of a solid electrolyte 81 which is subjected to gas to be monitored. Again, in the seventh embodiment, the pair of third electrodes 84a, 84b are partially embedded in a groove 81a formed in the surface of the solid electrolyte 81, like in the case of the sixth embodiment. Also, in the seventh embodiment, the second electrode 83 is provided like in the case of the sixth embodiment.

Figure 13:
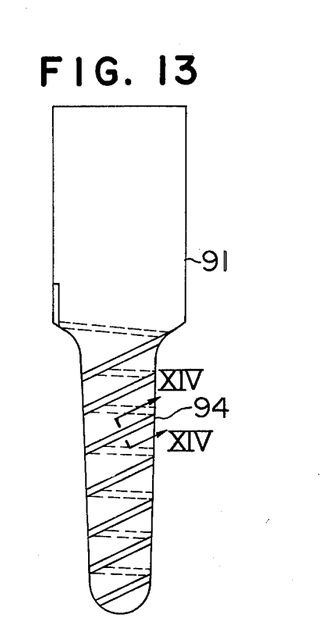
FIGS. 13 and 14 are front view and sectional view, respectively, showing a solid electrolyte in an eighth embodiment of the present invention.
Figure 14:
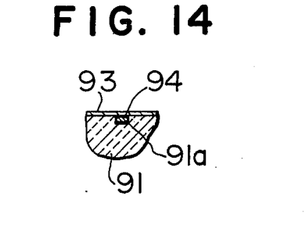

FIGS. 13 and 14 show an eighth embodiment of the present invention, in which a spiral electrode 94 of platinum wire is formed on a surface of a solid electrolyte 91. In the eighth embodiment, an entire structure of the electrode 94 is embedded in a groove 91a formed in the solid electrolyte 91, and covered by a second electrode 93.

Figure 15:
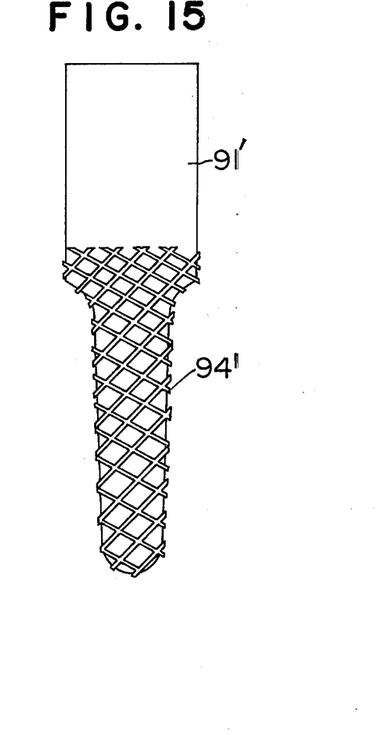
FIG. 15 is a front view showing a solid electrolyte in a ninth embodiment of the present invention.

FIG. 15 shows a ninth embodiment of the present invention in which a cup-shaped electrode 94' formed by a platinum wire net to present a contour of an outer periphery of a solid electrolyte 91' is firmly fitted onto the solid electrolyte 91'.

Figure 16:
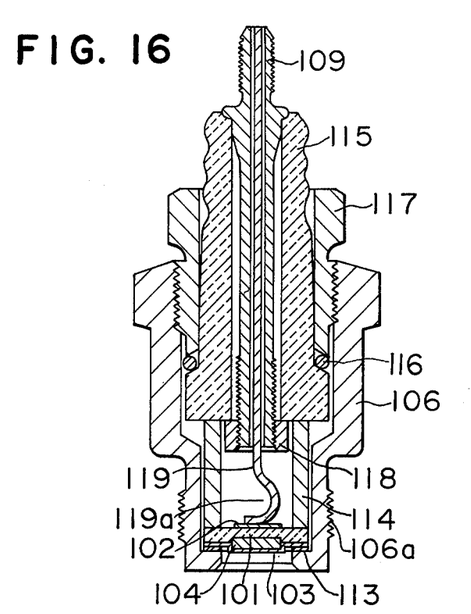
FIG. 16 is a front sectional view showing an overall arrangement of a tenth embodiment of the present invention.
Figure 17:
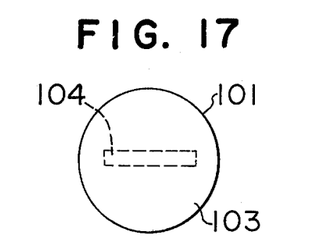
FIGS. 17 and 18 are plan view and sectional view, respectively, showing a solid electrolyte in the oxygen sensor of FIG. 16.
Figure 18:
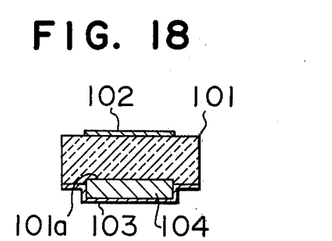

FIGS. 16 to 18 show a tenth embodiment of the present invention, which will not be described in detail.

An oxygen concentration detector 101 is of thin disc-shape, and first and second thin film electrodes of platinum 102 and 103 are formed on upper and lower surfaces of the disc, respectively, by vacuum deposition, chemical plating, sputtering or the like. A third wire-shaped electrode 104 made of a platinum wire is formed on that surface of the solid electrolyte 101 which is subjected to gas to be monitored, that is, on the bottom surface. A housing 106 is of cylinder shape and has a threaded portion 106a. The second electrode 103 electrically connects to the housing 106 through a ring-shaped conductive packing 113. A spacer ring, which is of cylinder shape, is pressed against the solid electrolyte 101 by an insulating member 115 having a communication hole. By screwing a conductive nipple 117 into the top portion of the housing 106 through the intervention of a conductive ring 116 fitted at a ramped portion of the insulating member 115, the latter is fixed in the housing 106 with the result that the solid electrolyte 101 is positively secured within the housing 106 by the spacer ring 114 and the insulating member 115. The housing 106 is threadedly coupled to the nipple 117. An inner shaft 109 made of a conductive metal has a through-hole and a threaded portion at the bottom thereof, which is adapted to be inserted into the communication hole of the insulating member 115 and tightened to the insulating member 115 by a nut 118 so that the inner shaft 109 is supported in the communication hole of the insulating member 115. A connecting pin 119 made of a conductive metal is inserted into the through-hole of the inner shaft 109 and fixed to a portion of the inner shaft 109. A tipend of a bent portion 119a a of the connecting pin 119 electrically connects to the first electrode 102. The measurement of an e.m.f. is carried out between the inner shaft 109 and the housing 106.

Figure 19:
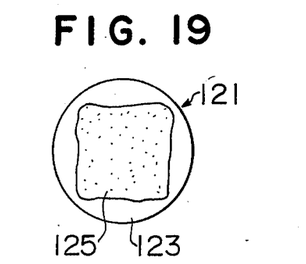
FIG. 19 is a plan view of a solid electrolyte in an eleventh embodiment of the present invention.
Figure 20:
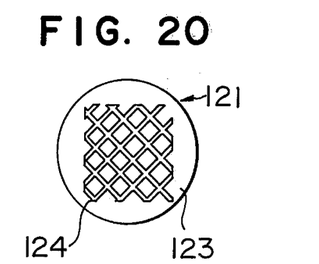
FIG. 20 is a plan view of FIG. 19 with an insulating coating 125 being removed.

FIGS. 19 and 20 show an eleventh embodiment of the present invention in which on that surface of a disc-shaped solid electrolyte 121 similar to that in the embodiment of FIG. 10, which is subjected to gas to be monitored, there is formed a planar wire net made of platinum wire to form a third electrode 124, and a coating 125 made of metal oxide, such as $\chi$-$Al_2O_3$, which is heat resisting and porous to permit the transmission of gas therethrough is formed on the surface of the third electrode 124 in order to prevent the peeloff of the third electrode 124. In the eleventh embodiment, like in the case of the tenth embodiment, a second electrode 123 is formed on the surface of the solid electrolyte 121 after the third electrode 124 has been formed. The coating 125 is formed on the surface of the third electrode 124 so that the second electrode 123 contacts with the packing 113 shown in the tenth embodiment.

In the tenth and eleventh embodiments, since the area of the second electrode is smaller than that of the first and second embodiments, the material of the electrode can be substantially saved and a cheaper solid electroltye can be provided.

In order to illustrate the effect of the present invention specifically, a comparison between the solid electrolyte of the present invention and a prior art solid electrolyte is given below. Samples I and II were prepared, for which various initial characteristics (prior to a durability test) under the measuring conditions described later were measured. Then, the durability test was performed under the test conditions described below, and the characteristics measured under the same measuring conditions after the durability test were compared with those measured prior to the test. (1) Measuring Conditions Engine: 6-cylinder, 2600 cc (with fuel injecting device) Engine Speed: 2000 r.p.m. Engine Vacuum: −120 mmHg Exhaust Gas Temperature: 650° C. Gasoline used: No lead added (2) Durability Test Conditions Engine: 4-cylinder, 1600 cc (with carburetor) Air-fuel ratio of mixture fed to engine: 13–14 Exhaust Gas Temperature: 570–890° C. Gasoline used: No lead added Test Period: 500 hours Under the above durability test conditions, the air-fuel ratio was adjusted to a value between 13 to 14 and the exhaust gas temperature was adjusted to a temperature between 570° and 890° C.

The solid electrolyte of the Sample I had a structure as shown in the sixth embodiment (with the third electrode 74), and the detector of the Sample II was similar to that of the Sample I except that the former had no third electrode.

Figure 21A:
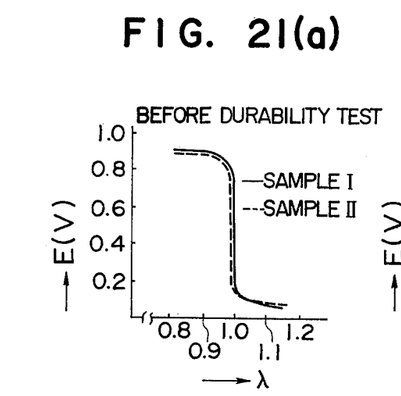
FIG. 21(a) shows a characteristic curve prior to a durability test and FIG. 21(b) shows that after the durability test.
Figure 21B:
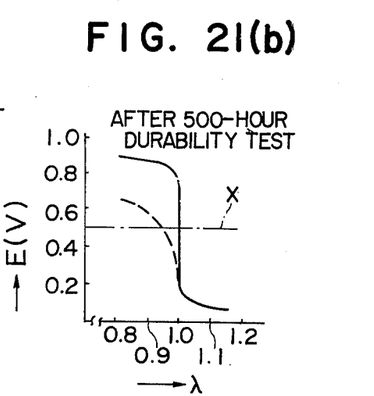

The results are shown in FIGS. 21 to 23. FIGS. 21(a) and 21(b) show characteristic curves illustrating a relation between an air excess ratio $\chi$ and an e.m.f. generated by the solid electrolyte. The air excess ratio $\chi$ is related to an air-fuel ratio and the air excess ratio $\chi$ of 1 corresponds to the stoichiometric air-fuel ratio. As seen from FIG. 21(a), prior to the durability test, both the Samples I and II exhibit a Z-shaped e.m.f. characteristic curve which abruptly changes near the point of $\chi - 1$. In FIG. 21(b) which shows the characteristics after the durability test, the Sample I shows no substantial change from the characteristic prior to the durability test, while the Sample II shows deformation of the Z-shaped characteristic curve to compare with that prior to the durability test. It is thus seen that when the reference voltage is set to e.g. 0.5 volt as indicated by a line X to maintain the stoichiometric air-fuel ratio, the detector of the Sample II is controlled to an air-fuel ratio which is richer than the stoichiometric ratio because of the deformation of its Z-shaped e.m.f. characteristic curve and cannot be accurately controlled to or near the stoichiometric ratio.

Figure 22A:
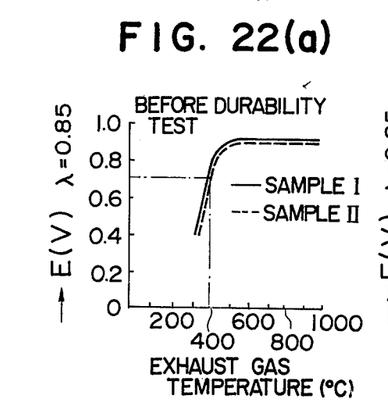
FIG. 22(a) shows a characteristic curve prior to a durability test and FIG. 22(b) shows that after the durability test.
Figure 22B:
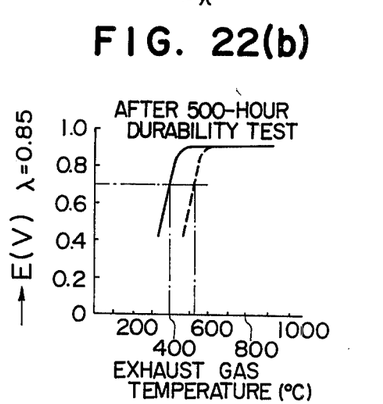

FIGS. 22(a) and 22(b) show characteristic curves illustrating a relation between an exhaust gas temperature and an e.m.f., and show how much temperature, at minimum, is required for the exhaust gas in order for an e.m.f. of 0.7 volts, which is necessary to maintain the air excess ratio to 0.85, to be generated. It is seen from FIG. 22(a) that prior to the durability test the Samples I and II have substantially the same characteristic in which the minimum temperature for attaining the e.m.f. of 0.7 volts is 400° C. In FIG. 22(b), the characteristic for the Sample I after the durability test remains substantially unchanged and the minimum temperature remains at 400° C., while the characteristic for the Sample II after the durability test shows substantial variation from that prior to the durability test with the minimum temperature being at 520° C. This means that when the exhaust gas temperature is low such as at a cool start of an internal combustion engine, the Sample II shows much poorer response than the Sample I.

Figure 23:
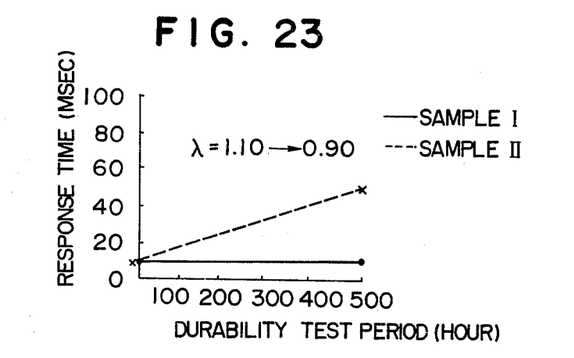
FIG. 23 shows a characteristic curve illustrating a relation between a response time and a durability test period for varying an air excess rate.

FIG. 23 shows characteristic curve for indicating the change of response time by the durability test, the response time being defined by a time period required to detect a response caused by changing the air excess ratio from 1.10 to 0.90. In FIG. 23, the response time for the Samples I and II prior to the durability test is 10 milli-seconds for both cases. After the 500-hour durability test, the response time for the Sample I is 10 milli-second, that is, remains unchanged. On the other hand, the response time for the Sample II increases in proportion with the period of the durability test and reaches about 50 milli-second after 500-hour durability test. This is much inferior to the case of the Sample I. This means that when the air excess ratio has changed from 1.10 to 0.90, the solid electrolyte of the Sample II still generates an e.m.f. corresponding to the air excess ratio of 1.10 and hence cannot maintain a proper air-fuel ratio.

As seen from FIGS. 21 to 23, the detector of the sixth embodiment shows much improved durability over the prior art solid electrolyte. Of course, this is due to the action of the third electrode of the wire-shaped rib structure.

The durability tests were carried out only for the structure of the sixth embodiment and not for the structures of other embodiments. However, it will be readily understood that the structures of other embodiments will also exhibit superior durability to that of the prior art detector. This has been proved by the inventors.

It should be understood that the application of the oxygen sensor according to the present invention is not limited to the detection of the air-fuel ratio of air-fuel mixture fed to an internal combustion engine by detecting oxygen concentration in the exhaust gas exhausted from the internal combustion engine but the present oxygen sensor may be applied to detect an oxygen concentration in combustion product exhausted from a combustion apparatus such as blast furnace or boiler for detecting an air-fuel ratio of mixture fed to the combustion apparatus (in order to enhance the heat efficiency, for example).

What is claimed is:

1. An oxygen sensor for sensing an oxygen content in exhaust gas exhausted from a combustion apparatus comprising:

a solid electrolyte made of an oxygen ion conducting metal oxide, said solid electrolyte having a first surface which is to be subjected to said exhaust gas and a second surface which is to be subjected to reference gas including oxygen gas and generating an e.m.f. corresponding to a difference between oxygen concentration in said reference gas;

a first electrode means disposed on said second surface of said solid electrolyte which is to be subjected to said reference gas;

a second electrode means of conductive wire-shaped member firmly bonded to said first surface of said solid electrolyte which is to be subjected to said exhaust gas; and a third electrode means of thin film disposed on those areas of said first surface of said solid electrolyte on which said second electrode means is not disposed and on an outer surface of said second electrode means.

2. An oxygen sensor according to claim 1 further including a heat resisting and porous insulating coating disposed to cover said third electrode means.

3. An oxygen sensor according to claim 2 wherein said coating is made of $\alpha$-alumina.

4. An oxygen sensor according to claim 2 wherein said insulating coating is made of a material selected from the group consisting of silicate of $ZrO_2$, MgO, $CaSiO_3$, $MgAl_2O_4$ having spinel structure, or composite oxide thereof, carbonate, nitrate or borate of metal, feldspar, kaolin, and sintered glass.

5. An oxygen sensor according to claim 1 wherein said second electrode means and said third electrode means are made of the same type of catalyst metal.

6. An oxygen sensor according to claim 1 wherein said second electrode means is made of metal wire.

7. An oxygen sensor according to claim 4 wherein said metal wire is arranged in spiral form.

8. An oxygen sensor according to claim 4 wherein said wire is arranged in mesh form.

9. An oxygen sensor according to claim 1 wherein said solid electrolyte is of plate shape.

10. An oxygen sensor according to claim 1 wherein said solid electrolyte has a composition consisting of 85 mole % of $ZrO_2$ and 15 mole % of CaO.

11. An oxygen sensor according to claim 1 wherein said solid electrolyte has a composition consisting of 90 to 92 mole % of $ZrO_2$ and 10 to 8 mole % of $Y_2O_3$.

12. An oxygen sensor according to claim 1, wherein said second electrode has a thickness of about 20 microns.

13. An oxygen sensor according to claim 12, wherein said third electrode has a thickness of about 1 to 2 microns.

14. An oxygen sensor according to claim 13 further including
a heat resisting and porous insulating coating formed on said third electrode for covering the same,
said heat resisting and porous insulating coating having a thickness of 50 to 200 microns.

15. An oxygen sensor for sensing an oxygen content in exhaust gas exhausted from an internal combustion engine and generating an e.m.f. to determine whether an air-fuel ratio of gas mixture fed to said internal combustion engine is richer or leaner than a stoichiometric ratio, comprising:
a solid electrolyte made of an oxygen ion metal oxide which generates an e.m.f. corresponding to a difference between an oxygen concentration in component gases of said exhaust gas and an oxygen concentration in reference gas;
a wire-shaped conductive rib made of a sintered structure of conductive metal particles and heat resisting bonding materials including glass frits or metal oxide frits, said rib being firmly bonded by said bonding material of said sintered structure to that surface of said solid electrolyte which is to be subjected to said exhaust gas; and
a porous thin film electrode of conductive metal disposed on an outer surface of said wire-shaped rib and on that surface portion of said solid electrolyte on which said wire-shaped rib is not disposed.

16. An oxygen sensor for sensing an oxygen content in exhaust gas exhausted from an internal combustion engine comprising:
a cylinder-shaped housing having an opening at one end thereof;
a disc-shaped solid electrolyte disposed near said opening of said housing;
said solid electrolyte being made of an oxygen ion conducting metal oxide having first and second surfaces, first surface being adapted to be subjected to said exhaust gas and second surface being adapted to be subjected to an atmosphere, said solid electrolyte generating either a small e.m.f. or a large e.m.f. depending on the absence or the presence of oxygen in said exhaust gas;
a porous thin film electrode disposed on said second surface of said solid electrolyte which is adapted to be subjected to the atmosphere;
a connecting pin having a bent portion electrically connected to said electrode to allow the derivation of said e.m.f.;
a wire-shaped conductive rib electrode firmly bonded to said first surface of said solid electrolyte which is adapted to be subjected to said exhaust gas; and
a porous thin film electrode disposed to cover said first surface of said solid electrolyte which is adapted to be subjected to said exhaust gas and an outer surface of said rib surface.

* * * * *